(12) United States Patent
Carmello et al.

(10) Patent No.: US 6,777,373 B1
(45) Date of Patent: Aug. 17, 2004

(54) CATALYST, PROCESS FOR ITS PREPARATION, AND ITS USE IN THE SYNTHESIS OF 1,2-DICHLOROETHANE

(75) Inventors: Diego Carmello, Mogliano Veneto (IT); Marco Garilli, Pordenone (IT); Pierluigi Fatutto, Mestre (IT); Letizia Caccialupi, Subbiano (IT)

(73) Assignee: EVC Technology AG, Zug (CH)

( * ) Notice: Subject to any disclaimer, the term of this patent is extended or adjusted under 35 U.S.C. 154(b) by 0 days.

(21) Appl. No.: 09/582,887

(22) PCT Filed: Jan. 6, 1999

(86) PCT No.: PCT/IB99/00065

§ 371 (c)(1),
(2), (4) Date: Jan. 6, 1999

(87) PCT Pub. No.: WO99/34918

PCT Pub. Date: Jul. 15, 1999

(30) Foreign Application Priority Data

Jan. 8, 1998 (EP) .............................. 98300097

(51) Int. Cl.⁷ ................................ B01J 23/70
(52) U.S. Cl. ...................... 502/346; 502/341
(58) Field of Search ............... 502/340, 345, 502/344

(56) References Cited

U.S. PATENT DOCUMENTS

| | | |
|---|---|---|
| 3,624,170 A | 11/1971 | Waklyama et al. ......... 260/659 |
| 4,446,249 A | 5/1984 | Eden ........................ 502/225 |
| 4,451,683 A | 5/1984 | Davies et al. ............... 570/224 |
| 4,460,699 A * | 7/1984 | Convers et al. .............. 502/84 |
| 4,802,974 A * | 2/1989 | Kukes et al. ............... 208/217 |
| 4,849,393 A | 7/1989 | Eden et al. ................. 502/225 |
| 4,908,343 A * | 3/1990 | Bhasin ....................... 502/218 |
| 5,260,247 A | 11/1993 | Helmut et al. .............. 502/225 |
| 5,292,703 A | 3/1994 | Young et al. ............... 502/303 |
| 5,380,697 A * | 1/1995 | Matusz et al. .............. 502/348 |
| 5,789,339 A * | 8/1998 | Ziebarth et al. ............ 502/303 |

FOREIGN PATENT DOCUMENTS

| | | |
|---|---|---|
| EP | 041330 | 12/1981 |
| EP | 119933 | 9/1984 |
| EP | 176432 | 4/1986 |
| EP | 0255156 | 2/1988 |
| EP | 0278922 | 8/1988 |
| EP | 0375202 | 6/1990 |
| GB | 971 966 | 12/1964 |
| WO | WO 81/01284 | 5/1981 |

* cited by examiner

*Primary Examiner*—Stanley S. Silverman
*Assistant Examiner*—Edward Johnson
(74) *Attorney, Agent, or Firm*—Woodcock Washburn LLP

(57) ABSTRACT

A catalyst is prepared by impregnating a γ-alumina support with a magnesium salt, drying the product, and impregnating the product with a copper salt, preferably together with a lithium salt. The catalyst preferably contains 0.1 to 5% magnesium, 2 to 10% copper and 0 to 5% lithium, by weight, and is particularly effective in oxygen-based processes.

2 Claims, 1 Drawing Sheet

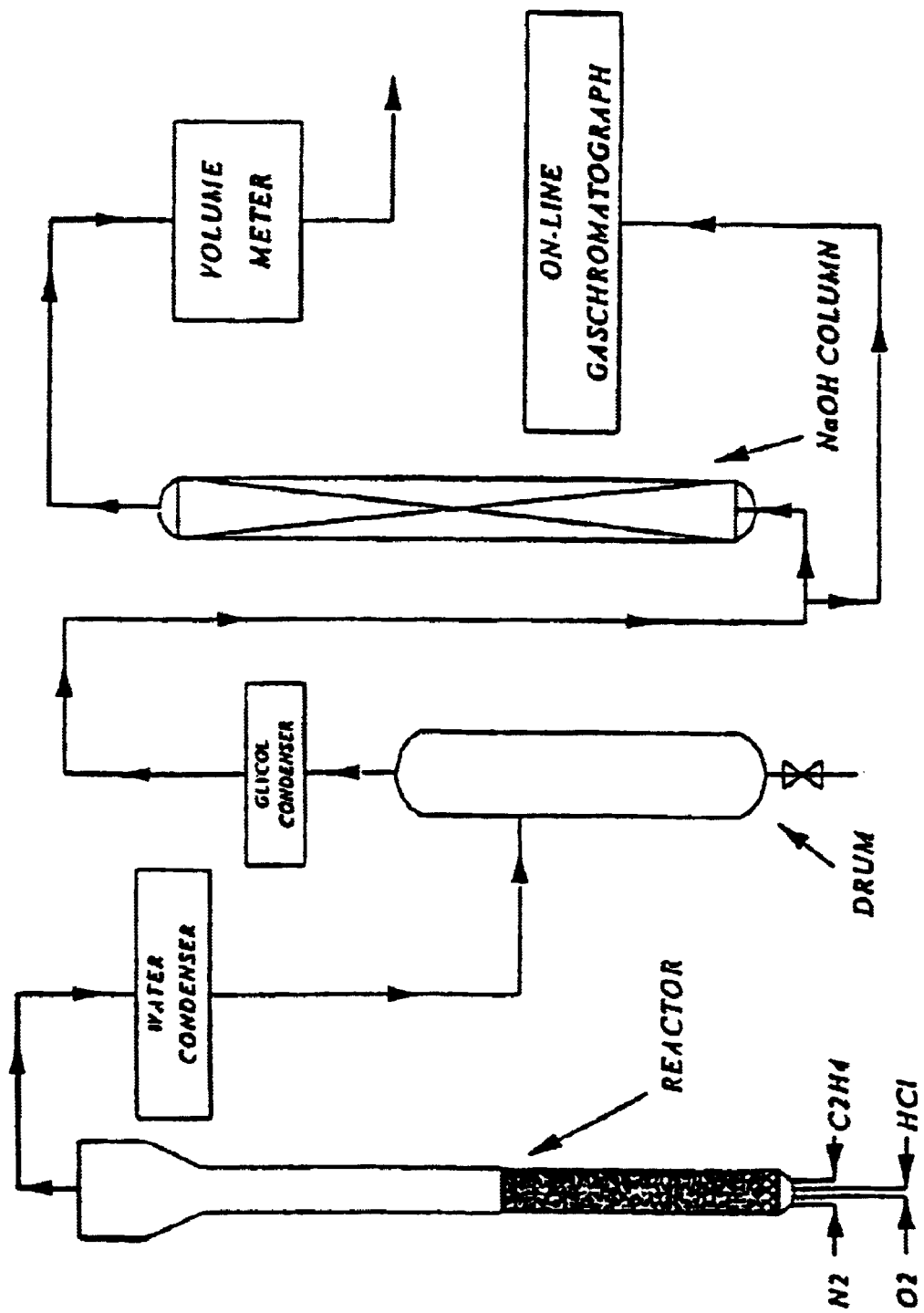

CATALYST, PROCESS FOR ITS PREPARATION, AND ITS USE IN THE SYNTHESIS OF 1,2-DICHLOROETHANE

INTRODUCTION

This invention relates to an industrial catalyst, its preparation, and its use, especially for the production of EDC by the oxychlorination of ethylene in a fluidizable or fixed bed reactor.

BACKGROUND OF THE INVENTION

The oxychlorination of ethylene to 1,2-dichloroethane (EDC) is known to be catalysed by catalysts containing, inter alia, copper, suitably in the form of its chloride, often in admixture with alkali metal salts, and carried on an alumina support. Such catalysts have been described, as well as the related preparation methods, in several patents. The ethylene oxychlorination reaction

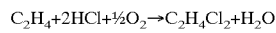

$$C_2H_4 + 2HCl + \tfrac{1}{2}O_2 \rightarrow C_2H_4Cl_2 + H_2O$$

exploits a catalyst whose active phase is copper chloride. The first patents claimed a simple catalyst prepared by impregnating a suitable support, often γ-alumina, with a solution containing copper chloride. However, a real development of such catalyst was achieved by adding a further salt, chosen from among the alkali, alkaline-earth or rare-earth metals. Thus, binary, ternary and sometimes quaternary compositions are described in many patents, as well as different preparation methods.

A typical example of a binary composition is described in EP 041330 (PPG) and is a catalyst prepared with copper and potassium chlorides. The claims refer to a real active phase constituted by $KCuCl_3$. The method of preparation is based on a co-precipitation of $CuCl_2$ and KCl on various supports, the preferred one being attapulgite clay. Copper content in the catalyst ranges from 4 to 12% by weight preferably between 7 to 9%. The molar ratio Cu:K is 1:1. Such a catalyst is said to be suitable for fluid bed applications.

European Patent EP 119933 (MONTEPOLIMERI) describes a binary composition based on copper and magnesium, codeposited on the support as chlorides. In this case, the preferred support is γ-$Al_2O_3$, preferably with a relatively high surface area and proper pore volume. The amount of copper in the catalyst lies in the range 1–10% by weight, while the magnesium content goes from 0 to 1 mole per mole of copper. The preparation method includes the use of HCl during the dry impregnation procedure.

European Patent EP 176432 (AUSIMONT) describes a fluidizable catalyst. Copper and magnesium are the metals used and the crucial item in the preparation method is said to be the radial distribution of the active phase inside the support particles. In fact, a catalyst having less copper on the surface of the particles is claimed, with relevant reduction of sticking phenomena. Copper and magnesium content in the catalyst falls between 1 and 10% by weight, preferably between 2 and 6% for copper.

In EP 0278922 (ENICHEM SYNTHESIS) is described a catalyst for fluid bed applications and the method for its preparation based on γ-alumina, Cu and alkali or alkaline earth metals. Copper content ranges from 3 to 7% by weight while from 0.01 to 4% of the aforesaid additives is included. The examples describe a γ-$Al_2O_3$-supported catalyst containing Cu and Ca; a catalyst containing also Mg; and a catalyst which includes Li instead of Mg. All the catalysts were prepared by one-shot impregnation, with an aqueous solution of the salts. The oxychlorination reactions are carried out using an air-based process, operating with an oxygen excess.

U.S. Pat. No. 4,446,249, (GEON) describes the use of a catalyst containing copper on γ-alumina, wherein the support is modified prior to the deposit of copper by incorporating in it from 0.5 to 3.0% by weight, based on the weight of the support, of at least one metal selected from the group consisting of potassium, lithium, rubidium, caesium, alkaline earth metals, rare earth metals and combinations thereof, by admixing a water solution salt of metal(s) with the γ-$Al_2O_3$, support, drying the mix and calcining it at 350 to 600° C. for about 4 to 16 hours. However, in the example in this patent, even though the Cl/C ratio settled is near the stoichiometric value and despite the excess of oxygen (about 60% above the stoichiometric) the HCl conversion to EDC is decidely low with respect to the usual standard conversion required by and achieved in modern industrial plants (>99%).

U.S. Pat. No. 3,624,170 (TOYO SODA) claims a ternary catalytic composition based on $CuCl_2$, NaCl and $MgCl_2$, the atomic ratio Cu:Na:Mg being 1:0.2–0.7:0.3–1.5. Such catalyst is claimed to avoid the deactivation caused by contamination due to $FeCl_3$ present inside the stainless steel reactors.

EP-A-0255156 (SOLVAY) describes ternary catalytic compositions containing a mixture of copper chloride, magnesium chloride and an alkali metal chloride which is sodium chloride or lithium chloride, used in precise proportions, which enable a good yield to be achieved in a fluidized bed process for the oxychlorination of ethylene to 1,2-dichloroethane, simultaneously reducing the corrosion of stainless steel reactors as a result, in particular, of a reduction in the sticking and clumping of the particles of catalyst. This document teaches that, for ternary compositions containing copper chloride, magnesium chloride and sodium chloride as an alkali metal chloride, a Na/Cu atomic ratio above 0.2:1 leads to problems of corrosion of the reactor. In contrast, if lithium is used as an alkali metal, no corrosion phenomenon is seen over a wide range of Li/Cu atomic ratios. However, the examples show the appearance of problems of sticking and clumping of the catalyst with compositions containing Li in an Li/Cu ratio above 0.6.

U.S. Pat. No. 4,849,393 (GEON) describes catalysts containing, besides copper chloride and an alkali metal salt, a rare earth metal salt. The catalysts contain from about 2% to about 8% by weight of copper, from about 1% to about 10% by weight of a rare earth metal salt and from about 0.25% to about 2.3% by weight of an alkali metal salt. All the salts are co-deposited on a suitable support by means of the dry impregnation procedure, to give a catalyst which allows high ethylene efficiency and low stickiness. In particular, it is stated that, using copper chloride, potassium chloride and one or more rare earth metal chlorides, an excellent catalyst for fluid bed ethylene oxychlorination is obtained.

More specific is the composition of the catalyst claimed in EP A 0375202 (ICI), in which is described a ternary catalytic composition based on copper chloride, magnesium chloride and potassium chloride. Copper content ranges from 3 to 9% by weight, while that of magnesium and potassium is from 0.2 to 3%. The preferred atomic ratios Cu:Mg:K are 1:0.2–0.9:0.2–09.

U.S. Pat. No. 5,260,247 (SOLVAY) describes a quaternary catalytic composition based on $CuCl_2$, $MgCl_2$, LiCl and at least one other alkali metal chloride on an inert support ($Al_2O_3$). Also in this patent the support is impregnated with the metal salts in one shot. The examples refer to an air-based oxychlorination process, operating with an oxygen excess of 36% and a Cl/C ratio of 0.95.

The catalytic activity of copper chloride supported on γ-alumina towards the oxychlorination of ethylene to EDC is thus well known and it is also known that several alkali metal salts or alkaline-earth metal salts improve the performance of the catalyst in terms of selectivity and productivity in fixed and fluid bed reactors. In the latter case, the fluidization is particularly critical, especially when the Cl/C ratio is close to 1, because in these conditions the HCl excess induces the phenomenon of stickiness. In the recycle process, where the ethylene is in excess with respect to the HCl, the problem of sticking is negligible and the final target is the maximum HCl conversion achievable operating with a low excess of oxygen, thus maximizing the ethylene yield to EDC. This is also true for fixed bed applications, characterized by a reactant stream very rich in ethylene.

As far as industrial fluid bed oxychlorination reactors are concerned, the main problems are related to: fluidization of the catalyst, abrasion of the reactor, ethylene yield to EDC and EDC productivity. In recycle processes, with which the present invention is particularly concerned, fluidisation of the catalyst is not a problem. Even abrasion of the reactor does not represent a critical item, because γ-alumina is usually used to prepare catalysts for fluid bed applications. However, any improvement in ethylene yield or in productivity is fundamental for an industrial application. It is, therefore the object of the present invention to provide a catalyst which is suitable for any oxychlorination reaction, air- or oxygen-based, and particularly for the oxygen-based process, which operates with vent gas recycle. Such a catalyst must lead to improved ethylene yield and productivity with respect to the existing industrial catalysts.

According to the present invention there is provided a catalyst which is suitable for catalysing the oxychlorination of ethylene to 1,2-dichloroethane, which comprises a γ-alumina support coated with a first layer containing magnesium and, on the first layer, a second layer containing copper and, optionally, lithium.

The invention also provides a process for preparing a catalyst suitable for catalysing the oxychlorination of: ethylene to 1,2-dichloroethane, which comprises impregnating γ-alumina with a solution containing a magnesium salt, drying the product, and impregnating the product with a solution containing a copper salt and, optionally, a lithium salt.

The catalyst suitably contains, by weight, from 0.1 to 5%, preferably 0.1 to 2%, magnesium; from 2 to 10%, preferably 2 to 8%, copper; and from 0 to 5%, preferably 0 to 1%, lithium. A particularly preferred catalyst contains, by weight, 0.5 to 1.5% magnesium; 3 to 6% copper; and 0.1 to 0.3% lithium.

The γ-alumina used as the catalyst support preferably is one having a surface area of from 50 to 220 m$^2$/g, especially 80 to 180 m$^2$/g, and an average particle size in the range 40 to 60 μm.

In a preferred process for producing the catalyst the γ-alumina is dried, in order to remove water adsorbed inside its pores, and is then impregnated with a solution of a magnesium salt, suitably magnesium chloride. The product is dried, suitably overnight, and it is then impregnated with a solution of a copper salt, suitably copper chloride, either alone or, preferably, in combination with a lithium salt, again suitably as lithium chloride. The product of this second impregnation step is then dried.

By pre-impregnating the γ-alumina with a magnesium salt the acidic centres on the alumina surface are neutralised, forming magnesium aluminate, and are thus unavailable for reaction with the copper. This means that all or substantially all of the copper is available for catalysing the oxychlorination reaction. This is demonstrated by the following solubility tests the results of which are given in Table 1.

TABLE 1

| SAMPLES | Cu (% w/w) Before Extraction | Cu (% w/w) After Extraction | Mg (% w/w) Before Extraction | Mg (% w/w) After extraction |
|---|---|---|---|---|
| Cu/Al$_2$O$_3$ | 4 | 3.52 | — | — |
| Cu/Mg/Al$_2$O$_3$ | 4 | 2.92 | 0.75 | 0.58 |
| Mg/Al$_2$O$_3$ | — | — | 0.75 | 0.74 |

Three catalysts were prepared by impregnating γ-alumina with 1) copper chloride, 2) copper chloride and magnesium chloride, and 3) magnesium chloride. The catalysts were treated with acetone, which is able to dissolve CuCl$_2$ and MgCl$_2$, but not copper or magnesium aluminate, nor the copper hydroxo-complexes, such as paratacamite Cu$_2$(OH)$_3$Cl. The catalyst containing only copper had its metal content reduced from 4 to 3.52%, while the presence of magnesium enhanced the amount of free copper chloride, leaving only 2.92% copper on the catalyst. At the same time, due to the competitive reaction between copper and magnesium to form the aluminate, part of the magnesium was present as chloride and dissolved in acetone, leaving 0.58% of that metal on the catalyst. Such competitive reaction is absent when there is no copper on the catalyst. In fact, all the magnesium added becomes insoluble (sample 3). It is to be noted that the amount of magnesium used for preparing the Mg/Al$_2$O$_3$ system was the same as was used for prearing the Cu/Mg/Al$_2$O$_3$ catalyst.

However, to have a catalyst not only active, but also giving a high productivity, a high dispersion of the active phase is required, i.e. very small crystals should be present all over the support surface. Big agglomerates do not help the catalyst action. Co-precipitation of CuCl$_2$ and MgCl$_2$ leads to the formation of macrocrystals, while the presence of lithium chloride produces microcrystals, enhancing the dispersion of the active phase. As a consequence, the preferred preparation method is as follows:

(i) impregnation of γ-alumina with a solution containing MgCl$_2$ (dry impregnation procedure);
(ii) drying at 80° C. overnight;
(iii) second impregnation with a solution containing CuCl$_2$ and LiCl followed by drying at 80° C. overnight;
(iv) activation of the catalyst at 200° C.

In experimental trials, the activation may be carried out directly inside the fluid bed pilot reactor.

The synergistic effect due to this preparation procedure provides a very efficient catalyst for ethylene oxychlorination, particularly for the oxygen-based process, which operates by recycling the vent gas and with low oxygen excess and low Cl/C ratios. This synergistic effect represents a substantial advantage over known methods. For example, in U.S. Pat. No. 4,446,249 (GEON), which describes a two-steps preparation procedure where the additive(s) are added prior to copper deposition, the method requires a calcination after the first impregnation, so that the support is modified through a reaction between the support and the alkali, alkaline-earth or rare earth metal salt(s). As a consequence, the support which is impregnated with the copper chloride solution has changed. Moreover, besides copper chloride no other salt is present in the solution used for the second dry impregnation.

On the contrary, the present invention is not based on a bulk modification of the support and a following simple impregnation with copper chloride, but rather modifies chemically only the surface of the support by means of magnesium aluminate formation and at the same time enhances the dispersion of copper, deposited in the second step together with lithium, whose ionic dimension induces the formation of highly dispersed small crystals.

BRIEF DESCRIPTION OF THE DRAWING

The attached FIGURE depicts a fluid bed pilot plant in which the catalyst described herein may be used to convert ethylene to 1,2-dichloroethane. This diagram is illustrative in nature and is not intended to be limiting, as those of skill in the art will recognize that the catalyst of the current invention may be used in any number of reactor configurations, including both fixed- and fluidized-bed reactors.

The following Examples are given to illustrate, but not to limit, the invention.

Experimental apparatus

All the experimental tests were carried out on the fluid bed pilot plant depicted in the FIGURE.

The core of such plant is the reactor, which is a tube made of nickel, 3 m length, with an internal diameter of 40 mm. Reagents flowrates are controlled by mass flow meters through a computer system which also keeps under control the whole pilot plant (pressure, temperature, etc). The products (EDC+water) are collected in a drum after condensation in a water condenser. Moreover, the vent gas from the first condenser undergoes a further cooling by means of a glycol condenser. The final vent gas is neutralized by a caustic washing, but such stream is analyzed by an on-line GC before neutralization. In fact the caustic washing removes the $CO_2$ present in that stream and this would not allow a correct mass balance. Finally, the amount of vent gas after the caustic column is measured. EDC and water collected in the drum are analyzed to give the EDC purity (identifying the impurities) and detect the amount of HCl unconverted, which dissolves in the water.

Catalyst preparation

All the catalysts were prepared following the dry impregnation procedure, i.e. by adding to the support a volume of solution equal to the total pore volume available.

In all the Examples, the support used for preparing the catalyst was a γ-alumina having a surface area of about 180 $m^2/g$, a pore volume of about 0.5 cc/g and a mean particle size of 45–50 μm. Such alumina was dried at 120° C. for 4 hours before the impregnation, in order to remove the water adsorbed inside the pores. Two kilograms of catalyst were prepared for each Example described below. The impregnation was carried out with solutions containing $CuCl_2$ and/or $MgCl_2$ and/or LiCl in amounts which ensure the final compositions reported in Table 2. The equipment used for the dry impregnation procedure was a rotary-vessel. After each impregnation, a drying step at 80° C. overnight was carried out. The activation was performed at 200° C. inside the pilot reactor under nitrogen flow. For all the samples the atomic ratios Cu:Mg:Li are 2:1:1.

Examples 1, 2, 4, 5, 7 and 9 are Comparative Examples.

TABLE 2

| EXAMPLE | Cu (% w/w) | Mg (% w/w) | Li (% w/w) | IMPREGNATION |
|---|---|---|---|---|
| 1 | 4 | — | — | Single |
| 2 | 4 | 0.75 | — | Single |
| 3 | 4 | 0.75 | — | Double |
| 4 | 4 | — | 0.2 | Single |
| 5, 7, 9 | 4 | 0.75 | 0.2 | Single |
| 6, 8, 10 | 4 | 0.75 | 0.2 | Double |

EXAMPLES 1–6

The catalysts were tested by using them in ethylene oxychlorination reactions carried out at the following operating conditions:

| | |
|---|---|
| temperature: | 220° C. |
| pressure: | 5 barg |
| residence time: | 17 seconds |
| $C_2H_4$ flow: | 150–160 Nl/h |
| HCl flow: | 250–260 Nl/h |
| $O_2$ flow: | 70–75 Nl/h |
| $N_2$ flow: | 240–250 Nl/h |

The results achieved under the aforesaid operating conditions are shown in Table 3:

TABLE 3

| EXAMPLE | Cl/C Ratio | O/C Ratio | HCl Conv. (%) | Recycle C2H4 yield (%) | EDC Purity % | Burning (%) |
|---|---|---|---|---|---|---|
| 1 | 0.81 | 0.48 | 99.59 | 95.89 | 99.18 | 2.39 |
| 2 | 0.8 | 0.48 | 99.83 | 96.55 | 99.38 | 1.97 |
| 3 | 0.82 | 0.47 | 99.56 | 97.47 | 99.46 | 1.43 |
| 4 | 0.79 | 0.48 | 99.93 | 96.46 | 99.23 | 1.9 |
| 5 | 0.8 | 0.49 | 99.86 | 97.66 | 99.43 | 1.25 |
| 6 | 0.79 | 0.48 | 99.86 | 97.88 | 99.48 | 1.07 |

From the above results it will be seen that there is a well defined catalyst activity sequence, taking into consideration the recycle ethylene yield as reference parameter. Such sequence is shown below:

Cu<Cu/Mg(s.i) and Cu/Li<Cu/Mg (d.i.)<Cu/Mg/Li(s.i)<Cu/Mg/Li(d.i)

Such sequence points out clearly that the effect due to the pre-impregnation with magnesium combined with the co-deposition of copper and lithium on the support is really positive and the synergistic effect associated with the double impregnation is quite evident. The average productivity of the catalyst achieved at these operating conditions is around 535 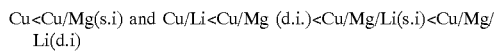.

EXAMPLES 7–8

Such Examples tested in the samples containing Cu, Mg and Li and were carried out to verify the effect of the double impregnation at different operating conditions. Thus, the temperature was increased by 5° C. and residence time was reduced by 2 seconds. Such test was devoted to study the catalyst behaviour when reactant flows are enhanced to gain in productivity. To balance the consequent residence time contraction the temperature was raised from 220 to 225° C. The overall operating conditions were:

| | |
|---|---|
| temperature: | 225° C. |
| pressure: | 5 barg |
| residence time: | 15 seconds |
| C$_2$H$_4$ flow: | 170–180 Nl/h |
| HCl flow: | 270–280 Nl/h |
| O$_2$ flow: | 75–80 Nl/h |
| N$_2$ flow: | 250–260 Nl/h |

The results achieved under the aforesaid operating conditions are shown in Table 4

TABLE 4

| EXAMPLE | Cl/C Ratio | O/C Ratio | HCl Conv. (%) | Recycle C2H4 Yield (%) | EDC Purity (%) | Burning (%) |
|---|---|---|---|---|---|---|
| 7 | 0.77 | 0.45 | 99.85 | 97.28 | 99.38 | 1.33 |
| 8 | 0.78 | 0.46 | 99.79 | 97.9 | 99.42 | 0.99 |

The results confirm that the Cu—Mg—Li based catalyst prepared by double impregnation is more efficient also at these operating conditions, reducing the ethylene loss by about 23%. Furthermore, the average productivity of the catalyst achieved is around 593 g$_{EDC}$/hkg$_{cat}$, that is about 11% higher with respect to Examples 1–6.

EXAMPLES 9–10

These tests focused on the catalyst flexibility, i.e. the ability of the catalyst to maintain a certain efficiency when residence time reduces without any increase in temperature. To do that, the reaction temperature was kept constant at 225° C., while residence time was reduced by 1 second with respect to Examples 7 and 8. The operating conditions settled were:

| | |
|---|---|
| temperature: | 225° C. |
| pressure: | 5 barg |
| residence time: | 14 seconds |
| C$_2$H$_4$ flow: | 180–190 Nl/h |
| HCl flow: | 290–300 Nl/h |
| O$_2$ flow: | 80–90 Nl/h |
| N$_2$ flow: | 280–290 Nl/h |

Even in this case, the double impregnation procedure ensures a higher ethylene yield, as shown in Table 5:

TABLE 5

| EXAMPLE | Cl/C Ratio | O/C Ratio | HCL conv (%) | Recycle C2H4 Yield (%) | EDC Purity (%) | Burning (%) |
|---|---|---|---|---|---|---|
| 9 | 0.78 | 0.45 | 99.91 | 97.41 | 99.4 | 1.29 |
| 10 | 0.77 | 0.44 | 99.96 | 97.7 | 99.34 | 1.1 |

The average productivity of the catalyst achieved at these operating conditions is around 648 g$_{EDC}$/h.kg$_{cat}$, which means an enhancement of ca.21% with respect to Examples 1–6 and ca. 9% in comparison with Examples 7–8. Thus, the oxychlorination catalysts of the present invention show substantial advantages over those previously proposed. The benefits reported in the Examples for pilot scale procedures represent very substantial savings when extrapolated to full-scale industrial production.

What is claimed is:

1. A process for preparing a catalyst comprising the steps of:
    (a) impregnating γ-alumina with a solution containing a magnesium salt;
    (b) drying the product of step (a); and
    (c) impregnating the product of step (b) with a solution containing a copper salt and, optionally, a lithium salt.
2. A process of claim 1 wherein said salts are chloride salts.

* * * * *